United States Patent

Haugwitz et al.

[11] 4,154,846
[45] May 15, 1979

[54] SUBSTITUTED THIO-, SULFINYL-, AND SULFONYL-ALKYL BENZIMIDAZOLE CARBAMATES

[75] Inventors: Rudiger D. Haugwitz; Frank L. Weisenborn, both of Titusville; Peter C. Wade, Pennington; Thomas P. Kissick, Princeton, all of N.J.

[73] Assignee: E. R. Squibb & Sons, Inc., Princeton, N.J.

[21] Appl. No.: 916,426

[22] Filed: Jun. 16, 1978

[51] Int. Cl.² .................. A61K 31/415; C07D 235/32
[52] U.S. Cl. .............................. 424/273 B; 548/306
[58] Field of Search ..................... 548/306; 424/273 B

[56] References Cited

U.S. PATENT DOCUMENTS

| | | | |
|---|---|---|---|
| 3,574,845 | 4/1971 | Acter et al. | 548/306 |
| 3,928,375 | 12/1975 | Düwel et al. | 424/273 B |
| 3,929,821 | 12/1975 | Beard et al. | 424/273 B |
| 3,929,823 | 12/1975 | Beard et al. | 548/306 |
| 3,954,791 | 5/1976 | Loewe et al. | 424/273 B |
| 4,002,640 | 1/1977 | Beard et al. | 548/306 |
| 4,025,638 | 5/1977 | Gyurik et al. | 424/273 B |
| 4,046,908 | 9/1977 | Haugwitz et al. | 548/306 |
| 4,076,828 | 2/1978 | Haugwitz et al. | 424/273 B |
| 4,093,732 | 6/1978 | Haugwitz et al. | 548/306 |

Primary Examiner—John M. Ford
Assistant Examiner—Natalia Harkaway
Attorney, Agent, or Firm—Lawrence S. Levinson; Merle J. Smith; Burton Rodney

[57] ABSTRACT

Benzimidazole carbamate derivatives are provided having the structure

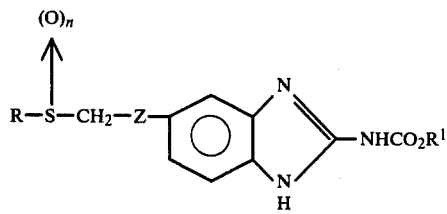

wherein R is lower alkyl, lower alkenylalkyl, lower alkynylalkyl, phenyl, substituted phenyl, cycloalkyl, cycloalkenyl, cycloalkylalkyl, cycloalkenylalkyl or phenylalkyl, $R^1$ is lower alkyl, phenylalkyl or di-lower alkylaminoalkyl, Z is a single bond or a straight or branched chain alkylene group, and n is 0, 1 or 2. These compounds are useful as anthelmintic agents administered orally or parenterally.

11 Claims, No Drawings

SUBSTITUTED THIO-, SULFINYL-, AND SULFONYL-ALKYL BENZIMIDAZOLE CARBAMATES

DESCRIPTION OF THE INVENTION

The present invention relates to benzimidazole carbamate derivatives which are useful in anthelmintic agents and have the structure

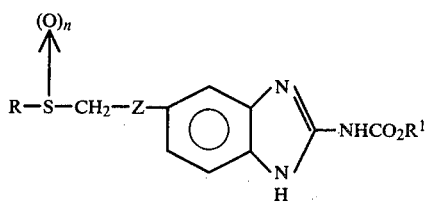

wherein R is lower alkyl, lower alkenylalkyl, phenyl, substituted phenyl, lower alkynylalkyl, cycloalkyl, cycloalkenyl, cycloalkylalkyl, cycloalkenylalkyl, or phenylalkyl, $R^1$ is lower alkyl, phenylalkyl or di-lower alkylaminoalkyl, Z is a single bond or a straight or branched chain alkylene group, and n is 0, 1 or 2.

The term "lower alkyl" or "alkyl" as used herein whether employed as an independent substitutent or as a part of another substituent includes straight or branched chain aliphatic hydrocarbon radicals having up to and including 7 carbon atoms, preferably 1 to 3 carbons, such as methyl, ethyl, propyl, isopropyl, butyl, isobutyl, t-butyl, amyl, hexyl, heptyl and the like.

The term "substituted phenyl" as used herein refers to a phenyl radical substituted with one or two groups, preferably one group including lower alkyl, hydroxy, nitro, halogen, lower alkoxy or trifluoromethyl.

The term "halogen" refers to Cl, Br, F or I, with Cl and Br being preferred.

The term "lower alkenylalkyl" refers to an unsaturated hydrocarbon groups having from 3 to 12 carbon atoms, preferably 3 to 6 carbons, and a single carbon-carbon double bond in a position other than the α-position, that is, not adjacent to the sulfur atom. Typical lower alkenylalkyl groups include, for example, 2-propenyl, 2-butenyl, 3-butenyl, and the like.

The term "lower alkynylalkyl" refers to an unsaturated hydrocarbon groups having from 3 to 12 carbon atoms, preferably 3 to 6 carbons, and a single carbon-carbon triple bond in a position other than the α-position, that is, not adjacent to the sulfur atom. Typical lower alkynylalkyl groups include, for example, 2-propynyl, 2-butynyl, 3-butynyl, and the like.

The term "phenylalkyl" as used herein refers to lower alkyl groups as discussed above having a phenyl substituent, such as benzyl.

The term "cycloalkyl" includes hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogen and/or 1 or 2 lower alkyl groups.

The term "cycloalkenyl" includes cyclic hydrocarbon groups containing 3 to 10 carbons, preferably 3 to 6 carbons. Examples of suitable cycloalkenyl groups include cyclopropenyl, cyclobutenyl, cyclohexenyl, cycloheptenyl, cyclononeyl and cyclodecenyl, any of which groups may be substituted with 1 or 2 halogen and/or 1 or 2 lower alkyl groups. In the above cycloalkenyl rings, the double bond may be at any position in the ring, other than the α-position, that is, not adjacent to the sulfur atom.

The terms "cycloalkylalkyl" and "cycloalkenylalkyl" as used herein refers to cycloalkyl groups and cycloalkenyl groups as defined above linked to a lower alkyl group as defined above.

Where "alkyl" is employed as a linking group to the sulfur atom, such as in lower alkenylalkyl, lower alkynylalkyl, cycloalkylalkyl, cycloalkenylalkyl and the like, the "alkyl" group in such cases is a straight or branched chain "alkylene" group containing from 1 to 7 carbons in the normal chain, such as, for example, $-CH_2-$, $-(CH_2)_2-$, $-(CH_2)_3-$, $-(CH_2)_4-$, $-CH_2-\underset{\underset{CH_3}{|}}{CH}-$, $-\underset{\underset{CH_3}{|}}{CH}-CH_2-$, $-CH_2-\underset{\underset{CH_3}{|}}{CH}-CH_2-$, $-CH_2-\underset{\underset{CH_3}{|}}{\overset{\overset{CH_3}{|}}{C}}-$, $-CH_2-\underset{\underset{CH_3}{|}}{CH}-CH_2-CH_2-$, $-\underset{\underset{CH_3}{|}}{\overset{\overset{CH_3}{|}}{C}}-$, $-CH_2-\underset{\underset{C_2H_5}{|}}{CH}-$, and the like.

The alkylene group Z will include any of the above alkylene groups containing from 1 to 4 carbons in the normal chain.

Preferred compounds of the invention are those wherein n is 0 or 1, R is lower alkyl, cycloalkyl, or cycloalkylalkyl, Z is a single bond or $CH_2$ or $(CH_2)_2$, and $R^1$ is lower alkyl or phenylalkyl.

Most preferred are compounds wherein R is lower alkyl, $R^1$ is lower alkyl, Z is a single bond and n is 0 or 1 or R is cycloalkylalkyl, $R^1$ is lower alkyl, Z is a single bond, and n is 0 or 1.

Thus, the compounds of the invention include the following:

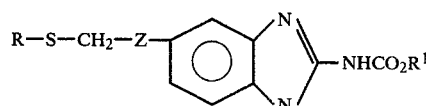

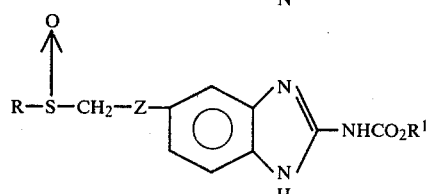

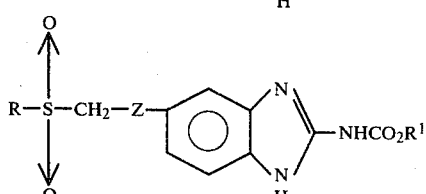

The compounds of the invention may be prepared according to the following procedures.

The compounds of formula I of the invention wherein n is 0 (that is, the sulfides of formula II) may be prepared by reacting a N-[4-hydroxyalkyl)-2-nitrophenyl]acetamide V with thionyl chloride

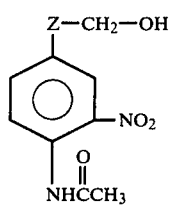

V in the presence of a solvent, such as dioxane, benzene, 1,2-dimethoxyethane, chloroform, tetrahydrofuran or other non-reacting solvent to form the corresponding chloride VI

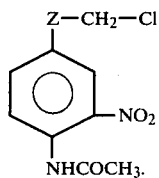

VI

The above chloride VI is separated from the reaction mixture and reacted with sodium methoxide and a thiol VII

RSH    VII in the presence of methanol, dioxane or other non-reacting solvent to form a 3-nitro-4-amino phenylalkyl sulfide of the formula VIII

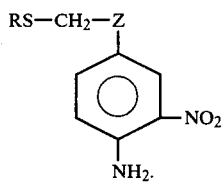

VIII

The 3-nitro-4-amino phenylalkyl sulfide VIII is then reduced to the corresponding diamine IX employing conventional chemical or catalytic techniques such as, for example, reaction with sodium dithionite in the presence of ammonium hydroxide, and ethanol or methanol or other non-reacting solvent

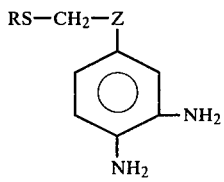

IX

The final step in the synthesis of I wherein n is 0, i.e., II, involves ring closure of the diamine IX. This may be achieved by refluxing of the diamine IX with a thiourea derivative X

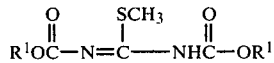

X in alcohols, such as methanol or ethanol.

The sulfoxide compounds of formula I, that is where n is 1, may be prepared by oxidizing the 3-nitro-4-amino phenylalkyl sulfide VIII with one equivalent of an oxidizing agent, such as m-chloroperbenzoic acid or peracetic acid to form a sulfoxide of the formula XI

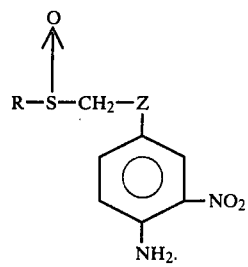

XI

The sulfoxide XI may then be reduced in a manner similar to that described above to the corresponding diamine XII

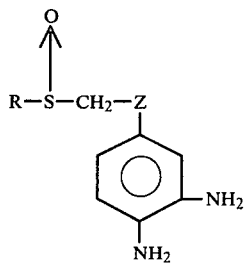

XII

The diamine XII may then be reacted with a thiourea derivative X in a manner similar to that described above to form the formula I compounds wherein n is 1 (that is III).

The formula IV sulfonyl compound of the invention (wherein n is 2 in formula I) may be prepared by oxidizing the 3-nitro-4-aminobenzyl sulfide VIII with two equivalents of m-chloroperbenzoic acid to form the sulfone XIII

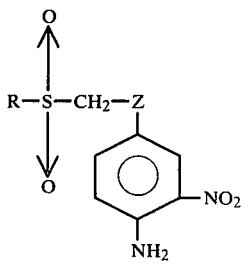

XIII which is then reduced to the corresponding diamine and the diamine reacted with the thiourea derivative X in a manner similar to that described above to form the formula IV sulfonyl compound of the invention.

The starting alcohol of formula V may be prepared from the corresponding carboxylic acid, namely, XIV

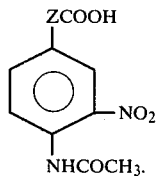

XIV

In preparing the alcohol V, the acid XIV is reacted with a chloroformate and the product is subjected to sodium borohydride reduction.

Alternatively, the sulfinyl compounds of formula III may be prepared by oxidizing thio compounds of formula II utilizing one equivalent of an oxidizing agent such as m-chloroperbenzoic acid, sodium m-periodate or hydrogen peroxide in acetic acid. Additional routes are outlined in Houben-Weyl's *Methoden Der Organischen Chemie*, Vol. 9, pp. 211–217 (1955), C Thieme Verlag, Stuttgart.

The sulfonyl compounds of formula IV may be prepared by oxidizing thio compounds of formula II utilizing two equivalents of an oxidizing agent as described above or by oxidizing sulfinyl compounds of formula III utilizing one equivalent of such oxidizing agent.

Various starting materials employed in the above reactions are either known in the art or easily prepared according to conventional techniques.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluene-sulfonate, and the like.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by Haemonchus, Ostertagia, Trichostrongylus, Cooperia, Dictyocaulus, Nematodirus, Bunostomum, Strongyloides, Oesophagostomum, Trichuris, Moniezia, and liver flukes (for example in sheep). In treating domesticated animals, the compounds are given orally; however, other routes such as parenterally, for example, subcutaneously, intravenously, interperitoneally and intramuscularly may be employed.

Where the compounds are administered orally, they may be mixed with a nontoxic, edible carrier to form a feed supplement, or may be administered in unit dosage forms such as powders, capsule, tablet, boluses, drenches, etc.

Where the compounds are administered parenterally, they may be dispersed (for example, suspended) in nontoxic non-pyrogenic physiologically acceptable carriers such as water, benzyl benzoate, 1,3-butylene glycol, ethyl oleate, glyceryl triacetate, castor oil, sesame oil, and sesame oil:benzyl benzoate (1:1). The parenteral product will usually take the form of a suspension containing from about 1 to about 10% by weight of the compound of formula I in anyone or mixture of the above carriers.

In general, the compounds of formula I exhbit anthelmintic activity when administered to animals (parenterally or orally) in a single dose of about 1 to about 150 mg per kilogram of animal body weight. It is preferred to employ in the range of 2.5–50 mg per kilogram of body weight. The compounds may be divided into a plurality of smaller doses given parenterally or orally over one or more days.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredient in a feed which is inert to said anthelmintic compounds so as to give feeds having concentrations of anthelmintic agent of from 0.1–2%.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

[5-[(Ethylthio)methyl]-1H-benzimidazol-2-yl]carbamic acid, methyl ester

A. N-[4-(Hydroxymethyl)-2-nitrophenyl]acetamide 8.3 ml (108 mmol) methyl chloroformate dissolved in 25 ml tetrahydrofuran (THF) is added dropwise over 15 minutes to a solution of 23.9 g (107 mmol) 4-(acetylamino)-3-nitrobenzoic acid and 14.8 ml (107 mmol) triethylamine in 150 ml dry THF under nitrogen and chilled in an acetone/ice bath. The temperature is kept below −5°. After stirring at −5° for 30 minutes, the triethylamine.HCl is filtered off and washed with 30 ml cold THF. The combined filtrates are added dropwise to a stirred solution of 10.3 g (108 mmol) sodium borohydride in 100 ml water chilled in an acetone/ice bath. The temperature is not allowed to exceed 15°. The resulting mixture is stirred at room temperature for 4 hours. After acidification with concentrated hydrochloric acid, the reaction mixture is taken up in ethyl acetate which is washed with water, 10% NaOH (X 2), water (X 2), dried ($Na_2SO_4$), and evaporated: 17 g. This material is crystallized from 20 ml methanol to give 9.1 g of the title compound, m.p. 114°–115°.

B. Ethyl-3-nitro-4-amino-benzyl-sulfide

Thionyl chloride (19.3 ml, 266 mmol) is added to 28.0 g (133 mmol) N-[4-(hydroxymethyl)-2-nitrophenyl]acetamide dissolved in 250 ml benzene and the mixture is stirred for 1 hour at 50°. The solvent is evaporated. The residue is washed with dioxane into a mixture of sodium methoxide (14.4 g, 266 mmol), ethanethiol (21.7 ml, 293 mmol), 100 ml methanol, and 150 ml dioxane. The mixture is refluxed for 1.5 hour, evaporated to one half volume and taken up in ethyl acetate which is washed with brine (X 3) and evaporated. The residue is refluxed in 250 ml methanol with 0.5 g sodium methoxide for 1.5 hours. The methanol is evaporated and the residue taken up in ethyl acetate which is washed with brine (X 2), dried ($Na_2SO_4$), and evaporated. The residue is dissolved in 100 ml ether to which 500 ml hexane is added. After stirring overnight at 0° the yellow solution is decanted from a dark oil and evaporated. The residue is chromatographed on a silica gel column (6.5×48 cm) eluted with ether/hexane (1:1). Fractions (20 ml) showing one spot on TLC with $R_f$ 0.59 (silica gel, ether/hexane 1:1) are combined and evaporated: orange oil is obtained which solidifies on standing overnight, to give the title B compound, m.p. 42°–44°, 10.6 g.

C. Ethyl 3,4-diaminobenzyl sulfide

A solution of sodium dithionite (2.05 g, 11.8 mmol) dissolved in 20 ml water and 5 ml concentrated ammonium hydroxide is added to the ethyl 3-nitro-4-aminobenzyl sulfide (1 g, 3.9 mmol) stirred in 20 ml 95% ethanol. The mixture is heated to reflux and 0.6 g sodium dithionite in 2 ml water and 0.5 ml ammonium hydroxide is added immediately. The mixture becomes colorless, is cooled to room temperature, basified with 5 ml 10% sodium hydroxide, evaporated to ½ volume, and washed with chloroform (X 5). The combined chloroform washings are washed with brine, dried ($Na_2SO_4$), and evaporated to give 0.65 g (92%) of an oil which is used without further purification.

D.
[[(Methoxycarbonyl)amino](methylthio)methylene]carbamic acid, methyl ester

To a solution of 112 g of 2-methyl-2-thiopseudourea sulfate in 200 ml of water at 0° C. there is added concurrently 260 ml of 25% NaOH and 160 ml of methyl chloroformate at such a rate that the pH remains between 7 and 8 as monitored by a pH meter. After the addition is complete the mixture is stirred for an additional 2 hours at room temperature. Then 400 ml of water is added and the mixture is extracted with dichloromethane. The organic layers are combined, dried over magnesium sulfate, and evaporated in vacuo to give a white solid. Crystallization from methanol yields 60.4 g of the title compound, m.p. 99°–101° C.

E.
[5-[(Ethylthio)methyl]-1H-benzimidazol-2-yl]carbamic acid, methyl ester

The diamine from part C is refluxed with the thiopseudourea from part D, (0.81 g, 3.94 mmol), 3 drops of acetic acid, and 25 ml methanol for 2 hours. A white precipitate forms which is stirred overnight at room temperature, filtered off, washed with methanol, and dried at 40° under vacuum to give 0.6 g of the title compound, m.p. 229°–231°.

EXAMPLE 2

[5-[(Ethylsulfinyl)methyl]-1H-benzimidazol-2-yl]carbamic acid, methyl ester 3.48 g (17.1 mmol) m-Chloroperbenzoic acid (85%) is dissolved in 50 ml chloroform and is added dropwise to 3.82 g (18.0 mmol) ethyl 3-nitro-4-aminobenzyl sulfide dissolved in 200 ml chloroform and chilled in an ice bath. Additional m-chloroperbenzoic acid is added in portions (0.2 g/5 ml chloroform) until starting sulfide disappears (by TLC:silica gel, hexane/ether 1:1). The reaction mixture is washed with saturated sodium bicarbonate, saturated salt solution, dried ($Na_2SO_4$), and evaporated.

To the residue dissolved in 100 ml 95% ethanol is added sodium dithionite (9.4 g, 54 mmol) dissolved in 60 ml water and 15 ml concentrated ammonium hydroxide. After refluxing for 5 minutes, portions of sodium dithionite (1 g in 10 ml water and 2 ml ammonium hydroxide) are added until the orange nitroaniline color disappears. The reaction mixture is reduced to one-half volume by evaporation, basified with 20 ml 10% sodium hydroxide, and extracted with chloroform (X 5). The chloroform washings are dried ($Na_2SO_4$) and evaporated. The residue, 3.3 g (16.1 mmol) of the thiopseudourea from Example 1, part D, 6 drops of acetic acid, and 50 ml of methanol are refluxed for 2 hours. After stirring overnight at room temperature, the product crystallizes out, is filtered off and digested with 50 ml hot methanol to yield the title compound, 2.77 g, m.p. 228°–235°(d).

EXAMPLE 3

[5-[(Ethylsulfonyl)methyl]-1H-benzimidazol-2-yl]carbamic acid, methyl ester 0.01 mole of [5-[(ethylthio)methyl]-1H-benzimidazol-2-yl]carbamic acid, methyl ester prepared as described in Example 1, is dissolved in 40 ml acetic acid and 40 ml chloroform, and cooled to −10° C. with an ice-methanol bath. To this is added 2 equivalents of m-chloroperbenzoic acid in 10 ml chloroform, all at once. Stirring is continued for three hours, allowing temperature to rise to room temperature. The solvent is removed in vacuo yielding an oil, which is digested with aqueous $NaHCO_3$. Solids are collected, washed with water, dried and crystallized from 1,2-dimethoxyethane to give the title sulfone.

EXAMPLES 4 to 21

Following the procedure of Example 1 but substituting for 4-(acetylamino)-3-nitrobenzoic acid, the acid shown in Column I of Table I set out below, substituting for ethanethiol, the thiol derivative shown in Column II and substituting for [[(methoxycarbonyl)amino](methylthio)methylene]carbamic acid, methyl ester, the compound shown in Column III, the product in accordance with the present invention shown in Column IV is obtained.

TABLE I

| | Column I | Column II | Column III | Column IV | | |
|---|---|---|---|---|---|---|
| | Z—COOH (benzene with NO2 and NHCCH3=O) | RSH | R¹—O—C(=O)—NH—C(=N—C(=O)—O—R¹)—S—CH₃ | R—S—CH₂—Z—(benzimidazole)—NHCO₂R¹ | | |
| Ex. No. | Z | R | R¹ | R | R¹ | Z |
| 4. | — | i-C₃H₇ | C₂H₅ | as in Column II | as in Column III | as in Column I |
| 5. | — | (cyclopropyl)—CH₂ | C₆H₅CH₂ | | | |
| 6. | CH₂ | CH₂=CH—CH₂ | CH₃ | | | |
| 7. | CH₂CH₂ | (CH₃)₂CHCH₂ | C₃H₇ | | | |
| 8. | CH₂CH₂CH₂ | CH≡C—CH₂ | (CH₃)₂NCH₂CH₂ | | | |
| 9. | CH₂ | (2,2-dichlorocyclopropyl)—CH₂ | C₆H₅CH₂ | | | |
| 10. | CH₂CH₂ | (cyclobutyl) | CH₃ | as in Column II | as in Column III | as in Column I |
| 11. | — | C₆H₅CH₂ | C₆H₅CH₂ | | | |
| 12. | —CH(CH₃)— | (2,2-dichloro-1-methylcyclopropyl)—CH₂ | (CH₃)₂N(CH₂)₂ | | | |
| 13. | —CH₂—CH(CH₃)— | (cyclohexyl) | CH₃ | | | |
| 14. | —CH₂—CH₂— | (CH₃)₂CHCH₂ | CH₃ | | | |
| 15. | —(CH₂)₃— | (cyclopropyl)—CH₂ | C₆H₅CH₂ | | | |
| 16. | —CH₂— | CH₂=CHCH₂ | C₆H₅CH₂ | | | |
| 17. | — | (cyclobutyl)—CH₂ | (C₂H₅)₂N—CH₂CH₂ | as in Column II | as in Column III | as in Column I |
| 18. | — | (2,2-dichlorocyclopropyl)—CH₂ | C₆H₅CH₂ | | | |
| 19. | — | CH₂=CH—CH₂ | CH₃ | | | |
| 20. | — | C₆H₅ | CH₃ | | | |
| 21. | CH₂ | p-Cl—C₆H₄ | C₂H₅ | | | |

EXAMPLES 22 to 39

Following the procedure of Example 2 but substituting for ethyl 3-nitro-4-aminobenzyl sulfide, the compound shown in Column I of Table II set out below, and substituting for [[(methoxycarbonyl)amino](methylthio)methylene]carbamic acid, methyl ester, the compound shown in Column II, the product in accordance with the present invention shown in Column III is obtained.

TABLE II

| | Column I | Column II | Column III | | |
|---|---|---|---|---|---|
| | R—S—CH₂—Z—(benzene with NO₂ and NH₂) | R¹—O—C(=O)—NH—C(=N—C(=O)—O—R¹)—S—CH₃ | R—S—CH₂—Z—(benzimidazole)—NHCO₂R¹ | | |
| Ex. No. | Z | R | R¹ | R | Z | R¹ |
| | | | | as in Column I | | as in Column II |
| 22. | — | i-C₃H₇ | C₂H₅ | | | |
| 23. | — | (cyclopropyl)—CH₂ | C₆H₅CH₂ | | | |
| 24. | CH₂ | CH₂=CH—CH₂ | CH₃ | | | |
| 25. | (CH₂)₂ | (CH₃)₂CHCH₂ | C₃H₇ | | | |
| 26. | (CH₂)₃ | CH≡C—CH₂ | (CH₃)₂NCH₂CH₂ | | | |

TABLE II-continued

| | | Column I R—S—CH$_2$—Z—(C$_6$H$_3$)(NO$_2$)(NH$_2$) | | Column II R$^1$—O—C(O)—NH—C(S—CH$_3$)=N—C(O)—O—R$^1$ | | Column III R—S(=O)(=O)—CH$_2$—Z—(benzimidazol-2-yl)—NHCO$_2$R$^1$ | | |
|---|---|---|---|---|---|---|---|
| Ex. No. | Z | R | R$^1$ | | R | Z | R$^1$ |
| 27. | CH$_2$ | Cl$_2$C$_3$H$_2$—CH$_2$ (gem-dichlorocyclopropylmethyl) | C$_6$H$_5$CH$_2$ | | | | |
| 28. | (CH$_2$)$_2$ | cyclopentyl | CH$_3$ | | | as in Column I | as in Column II |
| 29. | — | C$_6$H$_5$CH$_2$ | C$_6$H$_5$CH$_2$ | | | | |
| 30. | —CH(CH$_3$)— | Cl$_2$C$_3$(CH$_3$)—CH$_2$ | (CH$_3$)$_2$N(CH$_2$)$_2$ | | | | |
| 31. | —CH$_2$CH(CH$_3$)— | cyclohexenyl | CH$_3$ | | | | |
| 32. | (CH$_2$)$_2$ | (CH$_3$)$_2$CHCH$_2$ | CH$_3$ | | | | |
| 33. | (CH$_2$)$_3$ | cyclopropyl—CH$_2$ | C$_6$H$_5$CH$_2$ | | | | |
| 34. | CH$_2$ | CH$_2$=CHCH$_2$ | C$_6$H$_5$CH$_2$ | | | | |
| 35. | — | cyclobutyl—CH$_2$ | (C$_2$H$_5$)$_2$N—CH$_2$CH$_2$ | | | | |
| 36. | — | Cl$_2$C$_3$H$_2$—CH$_2$ | C$_6$H$_5$CH$_2$ | | | as in Column I | as in Column II |
| 37. | — | CH$_2$=CH—CH$_2$ | CH$_3$ | | | | |
| 38. | — | C$_6$H$_5$ | CH$_3$ | | | | |
| 39. | CH$_2$ | p-Cl—C$_6$H$_4$— | C$_2$H$_5$ | | | | |

EXAMPLES 40 TO 57

Following the procedure of Example 3 but substituting the compounds of Examples 4 to 21 for [5-[(ethylthio)methyl]-1H-benzimidazol-2-yl]carbamic acid, methyl ester as shown in Column 1 of Table III set out below, the corresponding sulfones shown in Column II are obtained.

TABLE III

| | | Column I R—S—CH$_2$—Z—(1H-benzimidazol-2-yl)—NHCO$_2$R$^1$ | | Column II R—S(=O)(=O)—CH$_2$—Z—(1H-benzimidazol-2-yl)—NHCO$_2$R$^1$ | | |
|---|---|---|---|---|---|---|
| Ex. No. | R | Z | R$^1$ | R | Z | R$^1$ |
| 40. | i-C$_3$H$_7$ | — | C$_2$H$_5$ | | as in Column I | |
| 41. | cyclopropyl—CH$_2$ | — | C$_6$H$_5$CH$_2$ | | | |
| 42. | CH$_2$=CH—CH$_2$ | CH$_2$ | CH$_3$ | | | |
| 43. | (CH$_3$)$_2$CHCH$_2$ | (CH$_2$)$_2$ | C$_3$H$_7$ | | | |
| 44. | CH≡C—CH$_2$ | (CH$_2$)$_3$ | (CH$_3$)$_2$NCH$_2$CH$_2$ | | | |
| 45. | Cl$_2$C$_3$H$_2$—CH$_2$ | CH$_2$ | C$_6$H$_5$CH$_2$ | | | |
| 46. | cyclopentyl | (CH$_2$)$_2$ | CH$_3$ | | as in Column I | |
| 47. | C$_6$H$_5$CH$_2$ | — | C$_6$H$_5$CH$_2$ | | | |

TABLE III-continued

| | Column I | | | Column II | | |
|---|---|---|---|---|---|---|
| Ex. No. | R | Z | $R^1$ | R | Z | $R^1$ |
| 48. | ![Cl Cl cyclopropyl with CH3] | $-\overset{CH_3}{\underset{|}{CH}}-$ | $(CH_3)_2N(CH_2)_2$ | | | |
| 49. | cyclohexyl- | $-CH_2\overset{CH_3}{\underset{|}{CH}}-$ | $CH_3$ | | | |
| 50. | $(CH_3)_2CHCH_2$ | $(CH_2)_2$ | $CH_3$ | | | |
| 51. | cyclopropyl-$CH_2$ | $(CH_2)_3$ | $C_6H_5CH_2$ | | | |
| 52. | $CH_2=CHCH_2$ | $CH_2$ | $C_6H_5CH_2$ | | | |
| 53. | cyclobutyl-$CH_2$ | — | $(C_2H_5)_2N-CH_2CH_2$ | | | |
| 54. | Cl Cl cyclopropyl-$CH_2$ | — | $C_6H_5CH_2$ | as in Column I | | |
| 55. | $CH_2=CH-CH_2$ | — | $CH_3$ | | | |
| 56. | $C_6H_5$ | — | $CH_3$ | | | |
| 57. | p-Cl-$C_6H_4$ | $CH_2$ | $C_2H_5$ | | | |

What is claimed is:

1. A compound of the structure

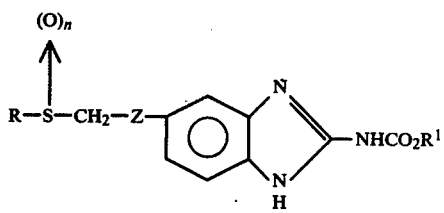

wherein R is lower alkyl, lower alkenylalkyl containing 3 to 12 carbons, phenyl, phenyl substituted with lower alkyl, hydroxy, nitro, halogen, lower alkoxy, or trifluoromethyl; lower alkynylalkyl containing 3 to 12 carbons, cycloalkyl, cycloalkenyl, cycloalkylalkyl, cycloalkenylalkyl or phenylalkyl, $R^1$ is lower alkyl, phenylalkyl or di-lower alkylaminoalkyl, wherein lower alkyl or alkyl alone or as part of another group contains 1 to 7 carbons, cycloalkyl alone or as part of another group contains 3 to 12 carbons, and cycloalkenyl alone or as part of another group contains 3 to 10 carbons, Z is a single bond or alkylene, and n is 0, 1 or 2, and physiologically acceptable salts thereof.

2. The compound as defined in claim 1 wherein n is 0.
3. The compound as defined in claim 1 wherein n is 1.
4. The compound as defined in claim 1 wherein R is lower alkyl, $R^1$ is lower alkyl, Z is a single bond, and n is 0 or 1.
5. The compound as defined in claim 1 wherein R is cycloalkylalkyl, $R^1$ is lower alkyl, Z is a single bond and n is 0 or 1.
6. The compound as defined in claim 1 having the name [5-[(ethylthio)methyl]-1H-benzimidazol-2-yl]carbamic acid, methyl ester.
7. The compound as defined in claim 1 having the name [5-[(ethylsulfinyl)methyl]-1H-benzimidazol-2-yl]carbamic acid, methyl ester.
8. An anthelmintic composition comprising a therapeutic amount of a compound as defined in claim 1 and a pharmaceutically acceptable carrier therefor.
9. A method for treating or preventing helminth infestation in mammalian hosts which comprises administering to a mammal a therapeutic amount of an anthelmintic composition as defined in claim 8.
10. The method as defined in claim 9 wherein said composition is administered orally or parenterally.
11. The method as defined in claim 9 wherein said composition is administered parenterally.

UNITED STATES PATENT OFFICE
CERTIFICATE OF CORRECTION

Patent No. 4,154,846            Dated May 15, 1979

Inventor(s) Rudiger D. Haugwitz et al.

It is certified that error appears in the above-identified patent and that said Letters Patent are hereby corrected as shown below:

Columns 11 and 12, Ex. 27., Column III should read

-- $\underbrace{R \quad Z}_{\text{as in Column I}} \quad \underbrace{R^1}_{\text{as in Column II}}$ --.

Column 11, Ex. 46, Column I, R, the structure should read

-- 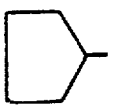 --.

Columns 13 and 14, Ex. 48 to 52, Column II should read

-- $\underbrace{R \quad Z \quad R^1}_{\text{as in Column I}}$ --.

Signed and Sealed this

Second Day of October 1979

[SEAL]

Attest:

RUTH C. MASON
*Attesting Officer*

LUTRELLE F. PARKER
*Acting Commissioner of Patents and Trademarks*